US00PP37846P3

(12) United States Plant Patent
Grosser

(10) Patent No.: US PP37,846 P3
(45) Date of Patent: Nov. 17, 2026

(54) MANDARIN PLANT NAMED 'C4-10-42'

(50) Latin Name: ***Citris* sp. This new cultivar is a complex mandarin hybrid containing *Citrus paradisi, Citrus clementina,* and *Citrus reticulata***
Varietal Denomination: C4-10-42

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/381,522

(22) Filed: Nov. 6, 2025

(65) Prior Publication Data

US 2026/0137013 P1 May 14, 2026

Related U.S. Application Data

(60) Provisional application No. 63/719,051, filed on Nov. 11, 2024.

(51) Int. Cl.
*A01H 5/08* (2018.01)
*A01H 6/78* (2018.01)

(52) U.S. Cl.
USPC ..... Plt./201
CPC ..... *A01H 6/785* (2018.05); *A01H 5/08* (2013.01)

(58) Field of Classification Search
USPC ..... Plt./201
See application file for complete search history.

(56) References Cited

U.S. PATENT DOCUMENTS

PP21,356 P3 10/2010 Gmitter, Jr. et al.
PP35,157 P2 * 5/2023 Carmi ..... A01H 6/785 Plt./202

* cited by examiner

*Primary Examiner* — Susan Mccormick Ewoldt
*Assistant Examiner* — Zachariah Allan Kay
(74) *Attorney, Agent, or Firm* — Koenig IP Works, PLLC; Katherine Koenig

(57) ABSTRACT

A new and distinct cultivar of orange plant named 'C4-10-42', a mid-season maturing seedless cultivar of *Citrus* (mandarin) for the fresh market. 'C4-10-42' a triploid hybrid with improved disease resistance to HLB and produces small, nearly seedless fruit with a sweet, rich flavor. Brix in the fruit is exceptionally high, and the fruit colors exceptionally well under Florida conditions (without cold-induction), both internally and externally. 'C4-10-42' is suitable for use in not-from-concentrate juice blends.

8 Drawing Sheets

Genus and species: *Citrus* sp. This new cultivar is a complex mandarin hybrid containing *Citrus paradisi, Citrus clementina*, and *Citrus reticulata.*

Cultivar denomination: 'C4-10-42'.

ACKNOWLEDGEMENT OF FEDERAL RESEARCH SUPPORT

N/A.

BACKGROUND OF THE NEW CULTIVAR

The present invention relates to a new and distinct cultivar of orange, botanically known as *Citrus* sp., and hereinafter referred to by the name 'C4-10-42'. This *Citrus* sp. is a member of Rutaceae.

The new *Citrus* (mandarin) cultivar 'C4-10-42' is a triploid hybrid from an interploid cross of diploid monoembryonic 'LB8-9' tangelo (U.S. Plant Pat. No. 21,356) (female parent) crossed with an allotetrapliod somatic hybrid of 'Nova' mandarin hybrid ('Clementine' x 'Orlando')+'Osceola' mandarin hybrid ('Clementine' x 'Orlando') (male parent), and was obtained via embryo rescue. 'Nova', 'Clementine', 'Orlando', and 'Osceola' are not patented. One original tree, planted in 2009 and grafted to 'Carrizo' citrange rootstock (unpatented), still exists and remains productive in Lake Alfred, Florida. True-to-typeness through propagation was demonstrated by topworking onto 'Swingle' citrumelo rootstock (unpatented) near Fort Meade, Florida.

SUMMARY OF THE INVENTION

The new cultivar 'C4-10-42', a mandarin hybrid, produces a small, nearly seedless 'Cutie'/'Halo' sized fruit with sweet, rich flavor. Fruit matures sometime between November and December, and holds into January. Brix in the fruit is exceptionally high, and can reach 18, including from a tree with long-term huanglongbing (HLB) infections (10+ years). Fruit colors exceptionally well under Florida conditions (without cold-induction), both internally and externally. Juice color can reach 42, with a very rich orange/red color (36 is the minimum color score for Grade A NFC orange juice). The fruit does not peel easily, similar to Florida juice oranges. Trees are highly tolerant of HLB. Because of the high brix and color and exceptional flavor, this selection has been identified as a candidate for legal 10% blending with not-from-concentrate (NFC) orange juice to improve the declining quality of Florida orange juice. Even at just 10%, the addition of juice from 'C4-10-

42' can improve the brix, color, and flavor of any NFC juice. Juice from 'C4-10-42' has excellent flavor that is not negatively affected by pasteurization, and had the highest flavor score of more than 240 selections in one trial conducted during the 2023-2024 season.

At this time there are no data supporting long-term field performance or yield for the new cultivar 'C4-10-42', although the original tree has remained productive when most of the surrounding hybrid trees have declined due to HLB and have been removed. The observed exceptional HLB tolerance was probably inherited from two of is highly HLB-tolerant parents, 'LB8-9' and 'Nova'. No obvious tree-debilitating disease problems have been observed in the trees or fruit currently grown. Alternate bearing has been observed in the original tree, but this issue has receded over time.

The new cultivar 'C4-10-42' can be compared to the commercial cultivar 'Page' (unpatented), which is a seedy diploid hybrid of 'Clementine' mandarin x 'Minneola' tangelo. Fruits of the new cultivar 'C4-10-42' are nearly seedless and slightly smaller than those of 'Page', the latter being seedy if the fruit is from cross-pollination. Both have a rich, sweet flavor. The new cultivar 'C4-10-42' displays strong HLB tolerances, whereas 'Page' is HLB-susceptible.

The new cultivar 'C4-10-42' can be compared to its female parent, 'LB8-9' tangelo, in that 'LB8-9' is a diploid plant, whereas 'C4-10-42' is a triploid plant. The new cultivar 'C4-10-42' can also be compared to its male parent, an allotetrapliod somatic hybrid of 'Nova' mandarin hybrid ('Clementine' x 'Orlando')+'Osceola' mandarin hybrid ('Clementine' x 'Orlando'), in that the male parent is a tetraploid plant, whereas 'C4-10-42' is a triploid plant. Both parents are seedy when cross pollinated, but 'C4-10-42' is nearly seedless. Further, 'C4-10-42' is not bell-shaped like 'LB8-9', and has smaller fruit than both parents. Leaf morphology is intermediate to that of the parent plants: tetraploid plants (including the male parent) generally have rounder, thicker leaves than diploid plants, and 'C4-10-42' has rounder, thicker leaves than 'LB8-9', but its leaves are less thick and round than the male parent. Tree vigor of 'C4-10-42' is also intermediate to that of the parent plants.

DESCRIPTION OF THE FIGURES

This new mandarin hybrid 'C4-10-42' is illustrated by the accompanying photographs which show the tree's from, foliage and fruit. The colors shown are as true as can be reasonably obtained by conventional photographic procedures. The photographs are of a tree approximately 15 years old. The colors (except those in common terms) are described from R.H.S. Colour Chart published by The Royal Horticultural Society in London (2007, 5th edition), in association with the Flower Council of Holland.

DETAILED BOTANICAL DESCRIPTION OF THE CULTIVAR

Figure 1:
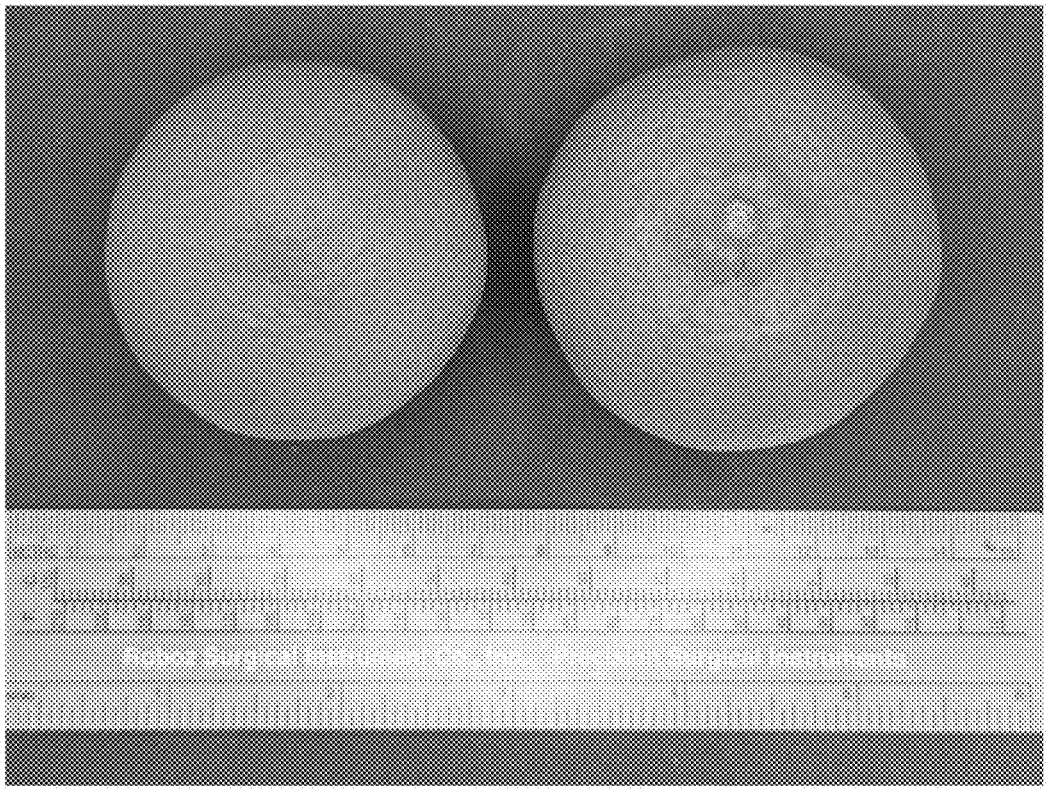
FIG. 1 shows whole fruit of the new cultivar 'C4-10-42', with a ruler shown for size reference.
Figure 2:
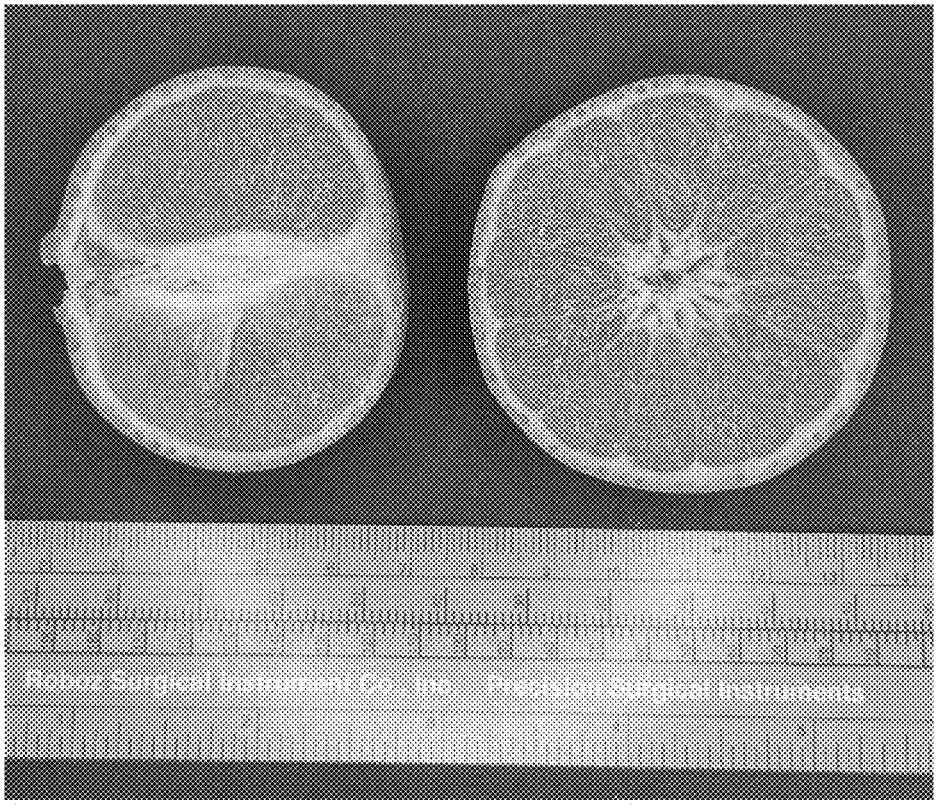
FIG. 2 shows cut fruit of the new cultivar 'C4-10-42', with a ruler shown for size reference.
Figure 3:
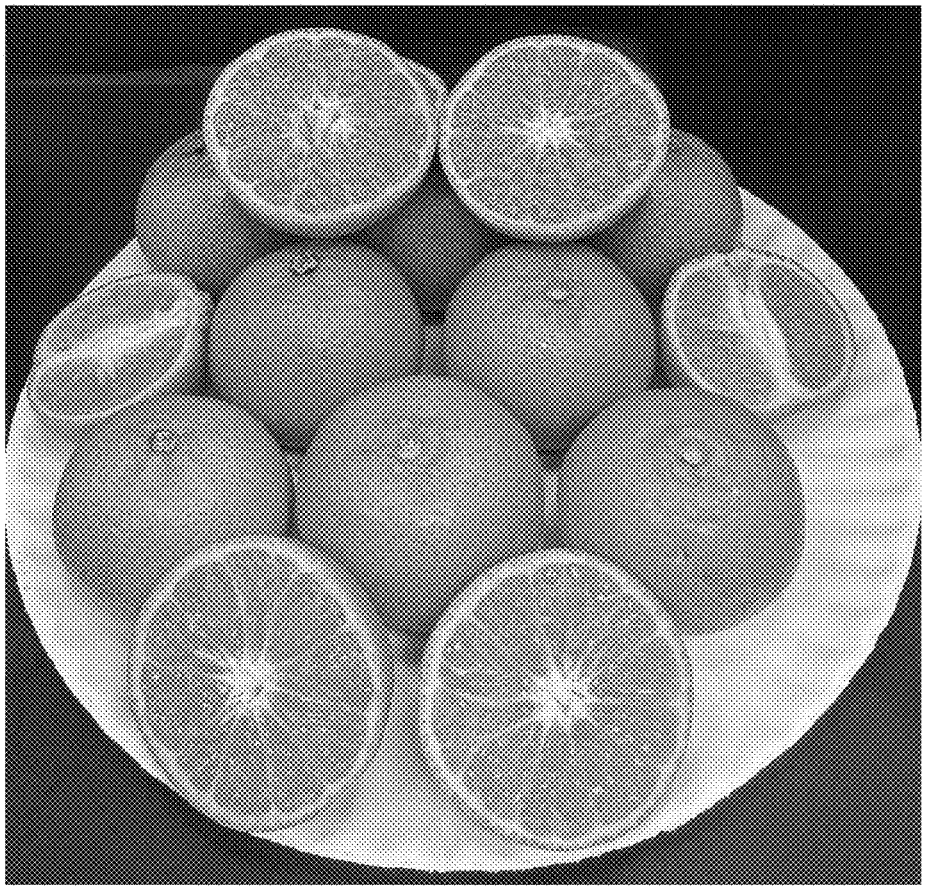
FIG. 3 shows whole and cut fruit of the new cultivar 'C4-10-42', with a ruler shown for size reference.
Figure 4:
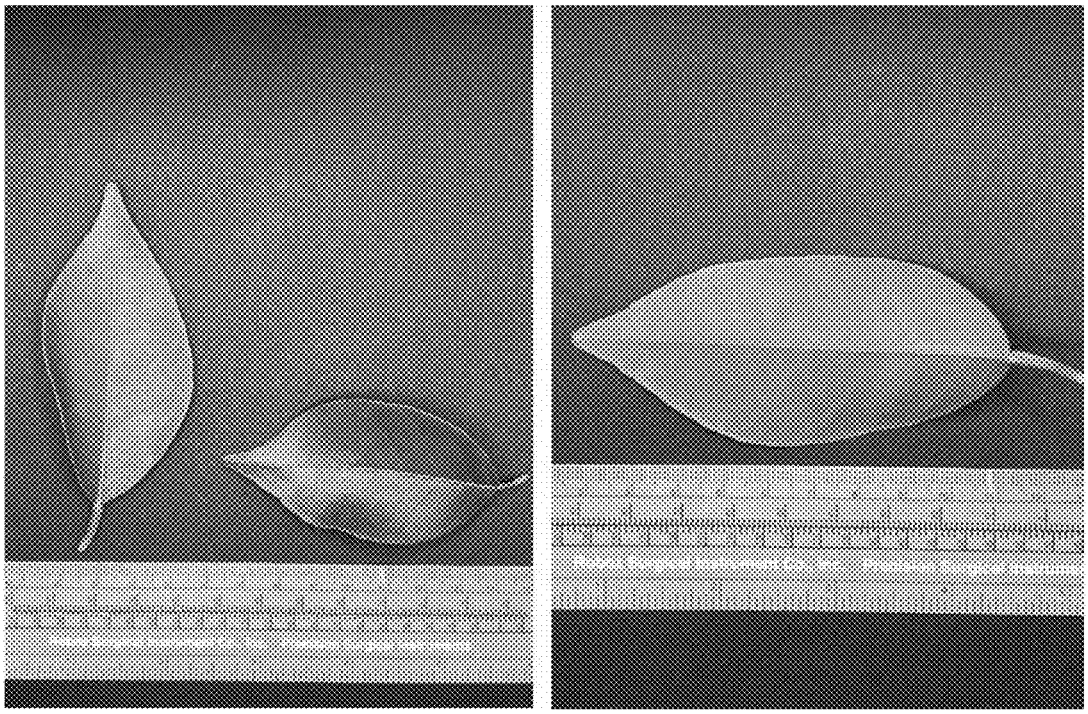
FIG. 4 shows upper and lower surfaces of leaves of the new cultivar 'C4-10-42', with a ruler shown for size reference.
Figure 5:
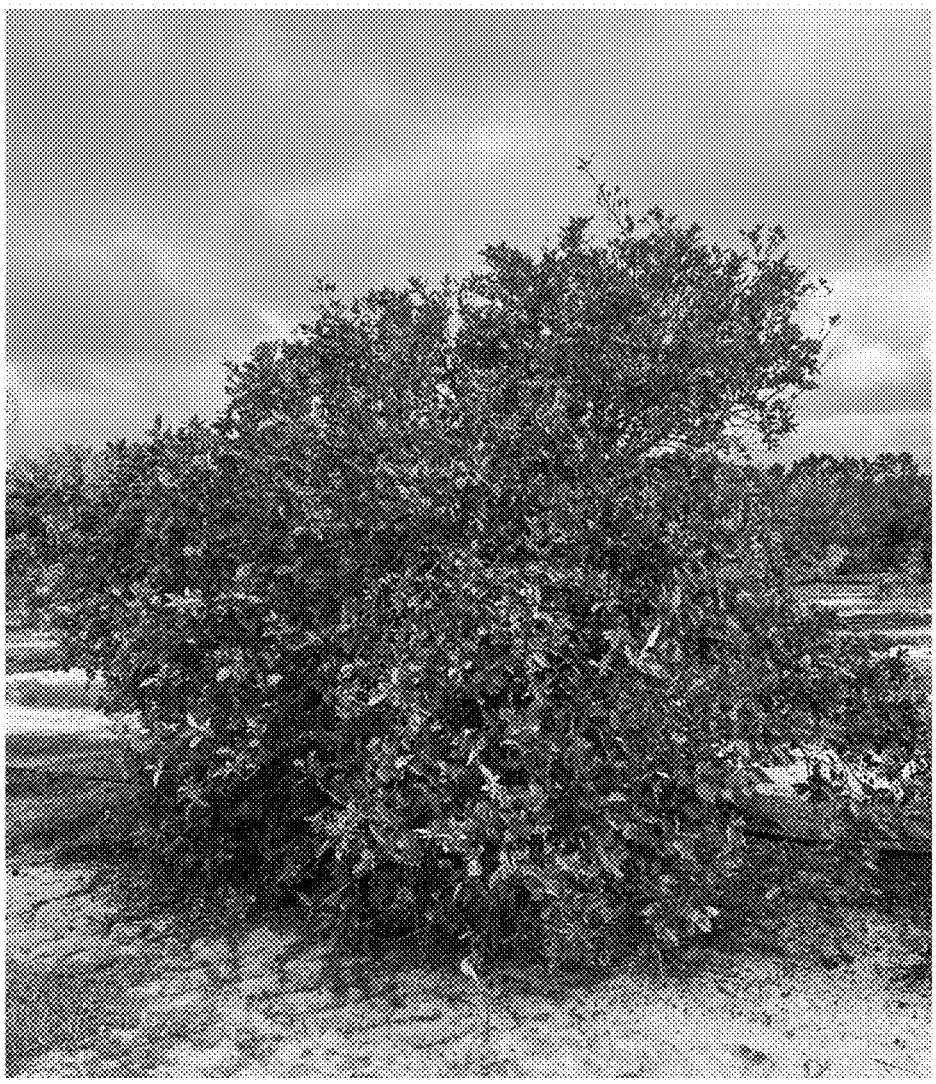
FIG. 5 shows the original tree of the new cultivar 'C4-10-42' planted near Lake Alfred, Florida, in 2009 (photo taken in August 2024)
Figure 6:
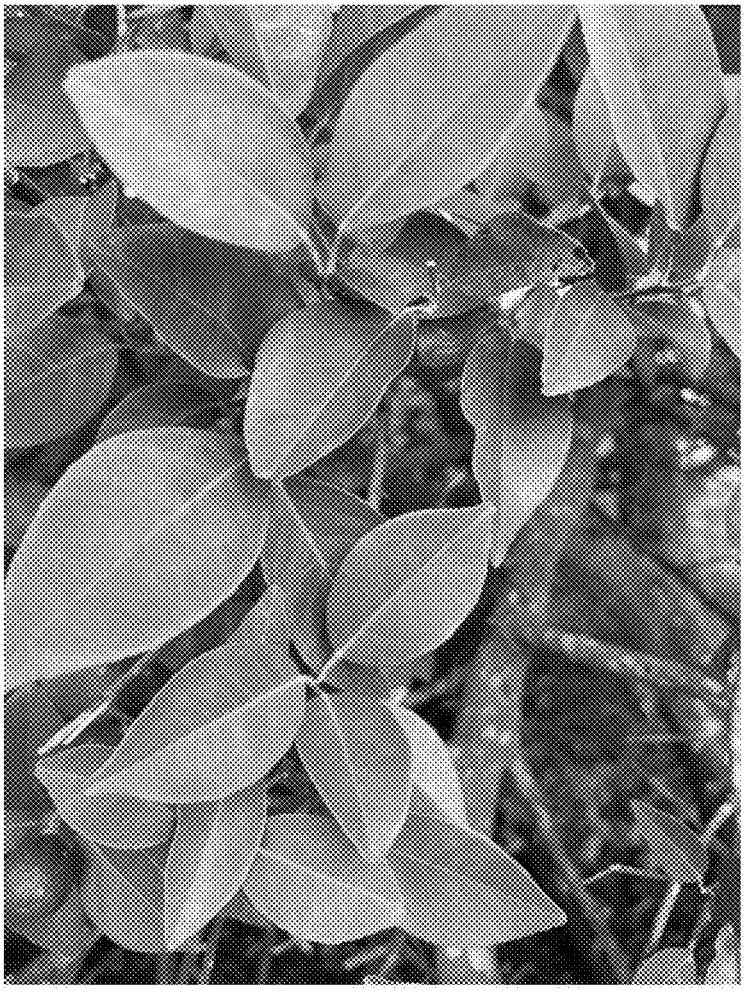
FIG. 6 shows leaves of the new cultivar 'C4-10-42' leaves on a tree.
Figure 7:
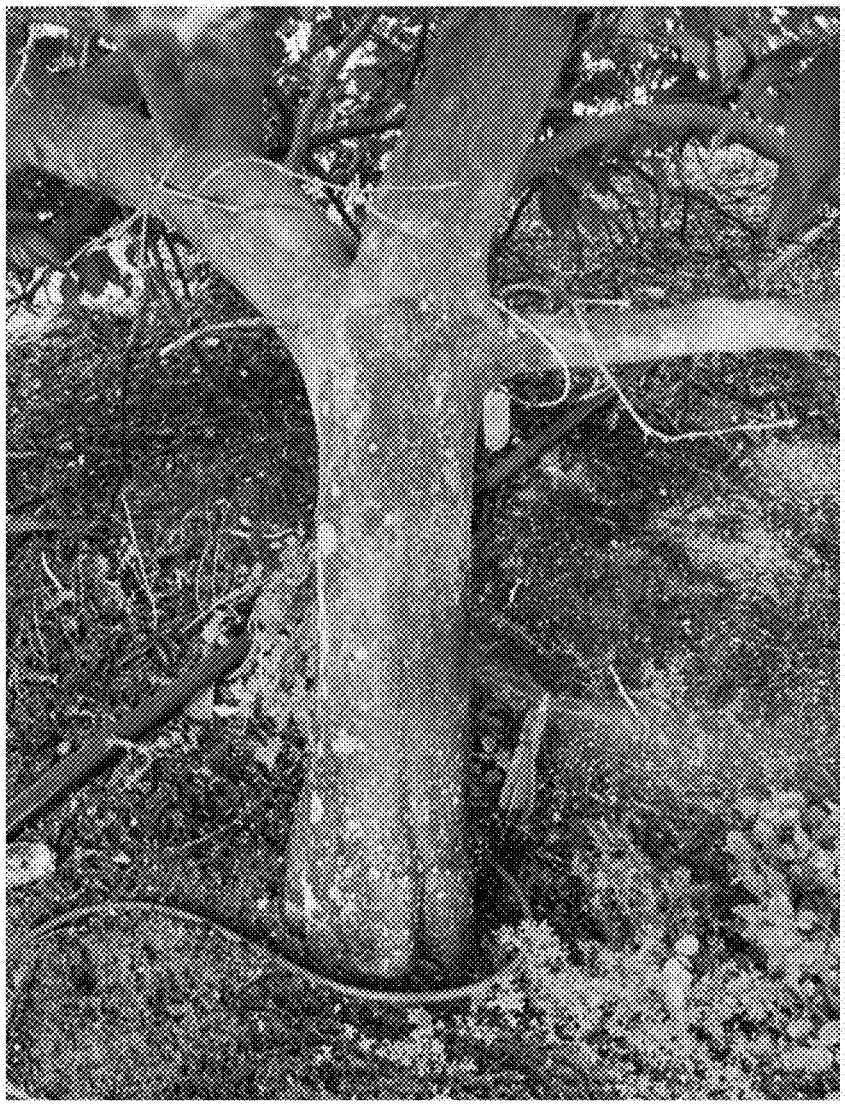
FIG. 7 shows a trunk and main scaffold branches of a tree of the new cultivar 'C4-10-42'.
Figure 8:
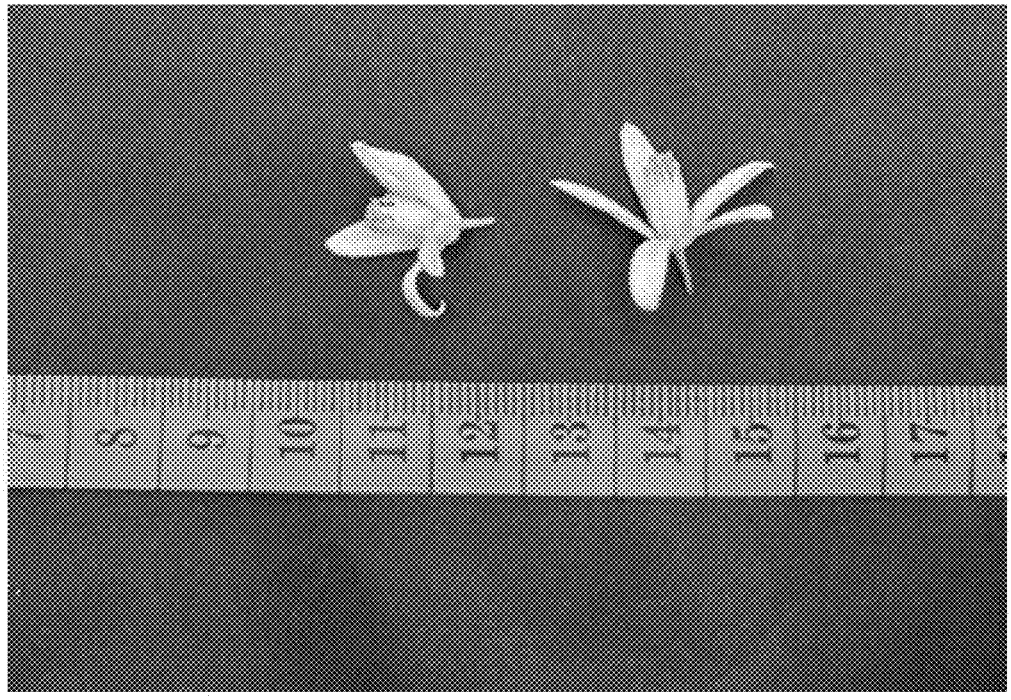
FIG. 8 shows fully expanded flowers of the new cultivar 'C4-10-42' with a ruler shown for size reference.

The following detailed description of 'C4-10-42' was obtained using seventeen-year-old plants grown in Lake Alfred, Florida.

Botanical Description

Botanical classification:

*Family*.—Rutaceae.

*Botanical name*.—*Citrus* sp. This new cultivar is a complex mandarin hybrid containing *Citrus paradisi, Citrus clementina*, and *Citrus reticulata*.

*Common name*.—Mandarin hybrid.

*Cultivar*.—'C4-10-42'.

Parentage: 'C4-10-42' is a triploid hybrid from an interploid cross of diploid monoembryonic 'LB8-9' tangelo (female parent) crossed with an allotetrapliod somatic hybrid of 'Nova' mandarin hybrid ('Clementine' x 'Orlando')+'Osceola' mandarin hybrid ('Clementine' x 'Orlando') (male parent).

Tree:

*Ploidy*.—Triploid.

*Size*.—Medium.

*Width across row*.—4.02 meters on average.

*Width down row*.—4.2 meters on average.

*Tree height*.—2.8 meters on average.

*Tree canopy diameter*.—13.10 meters on average.

*Vigor*.—High.

*Density*.—High.

*Tree shape* (*form*).—Spreading.

*Growth habit* (*current season*.—Rounded.

Trunk:

*Trunk diameter*.—43 cm at 30 cm above the ground on average.

*Trunk texture*.—Rough.

*Trunk bark color*.—RHS 201A (Grey Group).

Branches:

*Branch length*.—2.13 meters on average.

*Branch diameter*.—16.2 cm on average.

*Crotch angle*.—On average less than 90 degrees in the middle of the tree and some on the outside are more than 90 degrees (approximately 110-115 degrees).

*Branch texture*.—Less rough than the trunk.

*Branch color*.—RHS 200B (Brown Group).

Leaves:

Size (lamina average):

*Length*.—81.2 mm on average.

*Width*.—49.7 mm on average.

*L/W ratio*.—1.63 on average.

*Thickness*.—Relatively thick (approximately 0.2 mm).

*Type*.—Simple (unifoliate).

*Shape*.—Elliptical.

*Apex*.—Acute with the apex retuse.

*Base*.—Acute.

*Margin*.—Serrulate. Leaf edges with smaller, more evenly spaced serrations than a serrated leaf.

Surface:
*Upper surface*.—Smooth.
*Lower surface*.—Smooth.
Color:
*Upper surface* (*adaxial*.—RHS 141B (Green Group).
*Lower surface* (*abaxial*.—RHS 144A (Yellow-Green Group).
Petiole:
*Shape and attachment*.—Brevipetiolate. The junction between petiole and lamina is articulate.
*Shape* (*petiole wing*.—Obovate with a narrow end at the base.
*Length*.—10 mm on average.
*Width*.—2.2 mm on average.
*Color*.—RHS 144A (Yellow-Green Group).
Flowers:
*Type*.—Hermaphrodite.
*Flowers bearing*.—Single or cluster. Each cluster has 4-5 flowers. Some flowers can grow individually.
*Flower diameter*.—30 mm on average.
*Flower depth*.—15 mm on average.
*Flower blooming period*.—Late February to mid-March.
*First bloom*.—Usually late February.
*Full bloom*.—Usually early March.
*Fragrance*.—Fragrant.
Flower bud size:
*Length*.—0.8 mm for the initial visible flower bud; 12 mm for the mature flower buds before opened.
*Diameter*.—1 mm on average for the initial visible flower bud; 5 mm on the matured bud.
*Flower bud shape*.—Round.
*Flower bud color*.—RHS 142B (Green Group) for the initial visible flower bud; RHS 155D (White Group) for the mature buds.
Reproductive organs:
*Fertility*.—Self-fertile.
Petals:
*Number* (*per flower*).—5.
*Petal length*.—13 mm on average.
*Petal width*.—4 mm on average.
*Petal shape*.—Recurved/cruciform.
*Apex shape*.—Smooth with an obtuse angle.
*Base shape*.—Obtuse.
*Petal color*.—Upper surface: RHS 155C (White Group). Lower surface: RHS 155C (White Group). Margin: Smooth.
Sepals:
*Number* (*per flower*).—5.
*Shape*.—Delta shaped with an acute angle at the apex.
*Length*.—1 mm on average.
*Width*.—1 mm on average.
*Apex shape*.—Acute.
*Margin*.—Smooth.
*Sepal color*.—Upper surface: RHS 142D (Green Group). Lower surface: RHS 142B (Green Group).
Pedicel:
*Length*.—6 mm on average.
*Diameter*.—0.8 mm on average.
*Color*.—RHS 143B (Green Group).
Stamen:
*Number*.—23 per flower on average.
*Length*.—9.6 mm on average.
Anther:
*Length*.—1 mm on average.
*Width*.—0.5 mm on average.
*Pollen color* (*general*).—RHS 17A (Yellow-Orange Group).
Pistil:
*Number*.—1.
*Length*.—9 mm on average.
*Color*.—RHS 144D (Yellow-Green Group).
*Style length*.—8 mm on average.
*Style diameter*.—1 mm on average.
*Style color*.—RHS 144D (Yellow-Green Group).
*Ovary shape*.—Oval.
*Ovary diameter*.—3 mm on average.
*Ovary color*.—RHS 144B (Yellow-Green Group).
Fruit:
*Size*.—Relatively small.
*Average weight* (*per individual fruit*).—90 g on average.
*Length* (*height*).—50 cm on average.
*Diameter*.—55 cm on average.
*Shape*.—Obloid.
*Shape* (*cross-section*).—Obloid.
*Apex*.—Truncate.
*Base*.—Truncate.
Harvest:
*Date of first pick*.—Mid-November.
*Date of last pick*.—Early January.
Fruit stem:
*Length*.—25 mm on average.
*Diameter*.—2 mm on average.
*Color*.—RHS 137D (Green Group).
Rind:
*Adherence*.—Peelable (the bottom half adheres more tightly).
*Thickness*.—1 mm on average.
*Texture*.—Firm.
Color.—Flavedo (epicarp): RHS N30A (Orange-Red Group). Albedo (mesocarp): RHS 18D (Yellow-Orange Group).
*Style end*.—Closed.
*Rind oil cell density*.—50 cells/$cm^2$.
*Oil gland size*.—0.3 mm on average.
Flesh:
*Number of segments*.—10 on average.
*Segment length*.—50 mm on average.
*Segment width*.—12 mm on average.
*Juice*.—Abundant.
*Color*.—RHS N30B (Orange-Red Group).
*Texture*.—Soft.
Vesicles.—Thickness: Relatively thick. Length: 6 mm on average. Diameter: 2 mm on average.
Juice quality:
*Brix*.—13.6-18 (in trees having HLB).
*Acidity* (*average*).—0.9-1.1 (in trees with HLB).
*Ratio*.—12.5-20 (in trees with HLB).
*Juice color*.—39.6-42 (in trees with HLB).
*Lbs. solids/box*.—N/A.
Seeds:
*Number*.—1-3 seeds per fruit, with an average of 2.3 seeds per fruit.
*Fruit parthenocarpy*.—Yes.
Resistance to disease: Highly tolerant of HLB, no canker or other fruit rind diseases observed.

The invention claimed is:

1. A new and distinct mandarin plant named 'C4-10-42' as illustrated and described herein.

* * * * *